United States Patent [19]

Wakabayashi et al.

[11] Patent Number: 5,476,507
[45] Date of Patent: Dec. 19, 1995

[54] VASCULAR PROSTHESES

[75] Inventors: Sobei Wakabayashi; Tomoko Hashimukai, both of Fukui; Takeo Katakura, Ashigarakami, all of Japan

[73] Assignees: Terumo Kabushiki Kaisha, Tokyo; Seiren Co., Ltd., Fukui, both of Japan

[21] Appl. No.: 236,149

[22] Filed: May 2, 1994

Related U.S. Application Data

[63] Continuation of Ser. No. 841,557, Feb. 26, 1992, abandoned.

[30] Foreign Application Priority Data

Feb. 27, 1991 [JP] Japan .................................. 3-055802

[51] Int. Cl.⁶ .................................. A61F 2/04; A61F 2/06
[52] U.S. Cl. .................................. 623/1; 623/12; 600/36
[58] Field of Search .................................. 623/1, 11, 12; 600/36; 28/103, 104, 106, 116, 117, 121, 123; 57/204, 205, 243–248, 289

[56] References Cited

U.S. PATENT DOCUMENTS

| | | |
|---|---|---|
| 4,047,252 | 9/1977 | Liebig et al. |
| 4,226,079 | 10/1980 | Mountney et al. .................. 57/288 |
| 4,678,468 | 7/1987 | Hiroyoshi . |
| 4,792,336 | 12/1988 | Hlavacek et al. .................. 623/1 |
| 4,804,381 | 2/1989 | Turina et al. .................. 623/1 |
| 4,965,110 | 10/1990 | Berry .................. 623/1 |

FOREIGN PATENT DOCUMENTS

| | | |
|---|---|---|
| 0128741 | 6/1984 | European Pat. Off. . |
| 0179600 | 10/1985 | European Pat. Off. . |
| 0179600 | 4/1986 | European Pat. Off. .................. 623/1 |
| 0327903 | 1/1989 | European Pat. Off. . |
| 2339387 | 4/1976 | France . |
| 2635966 | 9/1989 | France . |
| 2222954 | 8/1989 | United Kingdom . |

OTHER PUBLICATIONS

Waden et al, "Matched Elastic Properties and Successful Arterial Grafting", *Arch Surg* vol. 115, (1980) 1166–1169.
Kinley et al, "Compliance: A continuing problem with vascular grafts", *J. Cardiovas Surg.*, 21, (1980) 163–170.
Okuhn et al, "Does compliance mismatch alone cause neointimal hyperplasia?", *J. Vascular Surg*, vol. 9, (1989) 35–45.

*Primary Examiner*—Debra S. Brittingham
*Attorney, Agent, or Firm*—Burns, Doane, Swecker & Mathis

[57] ABSTRACT

A vascular prosthesis is disclosed which excels in expansibility and allows satisfactory attachment thereto of cells and tissues. This vascular prosthesis is obtained by air-jet entangling a mass of yarns containing in at least a part thereof an elastic bulked yarn in order to get an entangled yarn furnished with fine crimps formed in fiber thereof, and fabricating a tubular fabric of the entangled fiber by one treatment selected from among weaving, knitting, and braiding treatments.

1 Claim, 3 Drawing Sheets

VASCULAR PROSTHESES

This application is a continuation of application Ser. No. 07/841,557, filed Feb. 26, 1992 now abandoned.

BACKGROUND OF THE INVENTION

1. Field of the Invention

This invention relates to a vascular prosthesis which is fabricated in a tubular shape of fibers and a method for the production thereof. More particularly, this invention relates to a vascular prosthesis which excels in elasticity and possesses characteristic qualities similar to those of a natural blood vessel capable of allowing ideal attachment thereto of cells and tissues and a method for the production thereof.

2. Description of the Prior Art

As the substitutes for natural blood vessels, the vascular prostheses made of woven and knit fabrics of polyester and expanded polytetrafluoroethylene have already been commercialized to date.

These vascular prostheses are directly implanted in patient's bodies and left standing therein for attaching cells and tissues thereto. Otherwise, at first in vitro vascular cells collected from host's natural blood vessels under an aseptic condition are attached to the vascular prostheses, then the cells attached vascular prostheses are implanted in patient's bodies and left standing therein for causing biological reactions of the attached cells and further attaching cells and tissues thereto.

For such vascular prostheses, what is important is the improvement in their patency. This requirement constitutes itself a particularly important task imposed on the development of a vascular prosthesis of a small diameter usable for transplantation of a peripheral artery. As one measure to improve the patency of a vascular prosthesis, the impartation to the artificial blood vessel of a physical property (elasticity) similar to that of a natural blood vessel subjected to transplantation may be cited (Waden R. et al.: Matched Elastic Properties and Successful Arterial Grafting, "Arch Surg.," Vol. 115, October 1980, pp. 1166 to 1169). In order that the patency of a vascular prosthesis particularly of the type having a small diameter may be enough to preclude thrombus on the inner wall surface of the vascular prosthesis and ensure the uniformity of the blood flow inside the anastomosed vascular prosthesis graft and the natural blood vessel, the vascular prosthesis is desired to possess a similar physical property (elasticity) with that of the corresponding natural blood vessel. Due to mismatch of physical property between the artificial and the natural blood vessel, the blood flow is disturbed possibly to the extent of causing thrombus particularly at the site of anastomotic end and consequently inducing intimal hyperplasia at the site of anastomotic end. It is held that the thrombus and the hyperplasia govern the lasting patency of the vascular prosthesis (Kinley CE et al.: Compliance: A continuing problem with vascular grafts, J. Cardiovas Surg 21: 163–170, 1980 or Okuhn SP et al.: Does compliance mismatch alone cause meointimal hyperplasia? J. Vascular Surg 9: 35–45, 1989).

As a way of imparting to a given vascular prosthesis the similar physical property with that of the natural blood vessel, the approach resorting to use of an elastic material has been in vogue. To be specific, a method which comprises preparing polyurethane as an elastic polymer and forming porous structure (Japanese Unexamined Patent Publication No. 182,958/1985, Japanese Patent Publication No. 11,861/1987, and Japanese Unexamined Patent Publication No. 183,757/1987), a method which comprises forming a multilayer porous structure by electrostatic spinning (Japanese Patent Publication No. 11,861/1987), and a method which comprises superposing porous sheets of nonwoven fabric (Japanese Unexamined Patent Publication No. 183,757/1987) have been proposed.

Further, for such vascular prostheses, the important matter is whether or not cells and tissues naturally existing in a host's body or cells and tissues extracted from a host's body and seeded are successfully attached to the outer and inner wall surfaces of the vascular prosthesis and allowed to gain in growth and eventually form a similar histologic structure with that of the host's own blood vessel.

For the purpose of ensuring fast attachment of the cells and tissues ideally, the practice of enhancing growth of the cells and tissues on the wall surfaces of the vascular prosthesis by forming loops on the wall surfaces of the vascular prosthesis which is made of fibers or by forming a finely porous texture in the wall of the vascular prosthesis which is made of a synthetic resin tube has been known.

For the formation of loops on the wall of a vascular prosthesis which is formed of a tubular fabric, for example, a method which, as disclosed in Japanese Patent Publication No. 14,823/1986, effects this formation of the loops in the production of the tubular fabric with a double raschel knitting machine by causing loop-forming yarns to be fed to the knitting machine at a larger speed than lattice-forming yarns has been known.

Another method which, as disclosed in Japanese Patent Publication No. 52,898/1988 covering an invention aimed at enhancing the proof of a knit fabric against fraying, accomplishes the formation of loops on the walls of a tubular fabric by subjecting this tubular fabric to a treatment with a high-pressure fluid thereby causing at least part of fibers intended for forming fluffs and/or loops to be twisted to fibers destined to form a matrix structure has been known.

When the vascular prosthesis is made of polyurethane, a substance which is capable of imparting to the product a similar physical property (elasticity) with that of a natural blood vessel, the produced vascular prosthesis indeed acquires an outstanding elasticity. However, when the polyurethane product is implanted to the body and left for a long period, the susceptibility of the polyurethane product to deterioration of the physical property has come to be unveiled (Tabata et al.: Clinical and experimental study on the insulation damage of polyurethane pacemaker leades, Jpn J Artif Organs 19(4), 1427–1431 (1990)).

The vascular prosthesis is an artificial internal organ which by nature is required to function permanently in vivo and is known to be inherently prone to the impact of water hammer stress arising from the harsh pulsative flow of blood. It must avoid deterioration in quality because this deterioration could cause aneurysm or dilation.

In accordance with the method disclosed in Japanese Patent Publication No. 14,823/1986 which comprises formation of loops on the wall surfaces of a vascular prosthesis, the produced vascular prosthesis has the disadvantage that the number of loops per unit surface area of the wall is small because one cycle of the needle motion produces only one loop. This vascular prosthesis, therefore, cannot sufficiently allow fast attachment of cells and tissues to the walls thereof. In accordance with the method disclosed in Japanese Patent Publication No. 52,898/1988, no sufficient intertwisting of fibers is obtained if the pressure of injection of the high-pressure flow is unduly small, and unnecessary breakage of surface fibers ensues and overall pressureproof of tube declines if this pressure is unduly large. Moreover, this method has the disadvantage that adjustment of the pressure of injection is not easy, application of uniform pressure on tubular fabric is difficult, and formation of loops is liable to result in disruption of uniformity of production. This method, therefore, encounters difficulty in obtaining a vascular prosthesis possessed of desired characteristic properties.

Improvements have been given to vascular prostheses which are made of a woven or knit fabric of polyester fibers represented by Dacron (Du Pont's proprietary product) and impartation of softness to such vascular prostheses has been accomplished successfully by adoption of extremely fine fibers. In the vascular prosthesis formed of these polyester fibers, impartation of elasticity has not been realized.

SUMMARY OF THE INVENTION

An object of this invention, therefore, is to provide a novel vascular prosthesis and a method for the production thereof. Another object of this invention is to provide a vascular prosthesis which possesses a physical property (elasticity) similar to that of a natural blood vessel, excels in the patency, and allows ideal attachment thereto of cells and tissues and a method for the production thereof. A further object of this invention is to provide a vascular prosthesis which long persists stably within vital tissues without inducing any deterioration of quality and functions with increased reliability and a method for the production thereof.

In a vascular prosthesis fabricated in a tubular shape by subjecting yarns to one treatment or a combination of two or more treatments selected from among weaving, knitting, and braiding treatments, the objects described above are accomplished by using as the yarns mentioned above an entangled yarn having fine crimps formed in fibers thereof, wherein the entangled yarn is prepared by air-jet entangling one or more species of elastic yarns subjected to a bulking treatment, a combination of one or more species of elastic yarns subjected to a bulking treatment with one or more species of elastic yarns not subjected to a bulking treatment, or a combination of one or more species of elastic yarns subjected to a bulking treatment with one or more nonelastic yarns subjected or not prior to the aforementioned weaving, knitting, and/or braiding treatments for tubular fabrication.

The objects described above are further accomplished by a vascular prosthesis fabricated in a tubular shape by subjecting yarns to one treatment or a combination of two or more treatments selected from among weaving, knitting, and braiding treatments, which vascular prosthesis is characterized by using as the yarn mentioned above an entangled yarn prepared by combining an elastic yarn as a core with an elastic yarn or a nonelastic yarn wrapped around the core, the vascular prosthesis exhibiting an elongation ratio in the range of from 2 to 15% in the radial direction and an elongation ratio in the range of from 2 to 20% in the axial direction under the load of an inner pressure of 150 mmHg.

In the vascular prosthesis of one embodiment of this invention, the aforementioned elastic yarns are yarns whose elongation ratio required for limiting the elastic recovery ratio from elongation below 90% is not less than 2% and the aforementioned nonelastic yarns are yarns whose elongation ratio required for limiting the elastic recovery ratio from elongation below 90% is less than 2%. In the vascular prosthesis of one preferred embodiment of this invention, the aforementioned elastic yarns and/or nonelastic yarns are polyester type yarns. In another preferred embodiment of this invention, the aforementioned entangled yarns are those which are obtained by entangling at least one species of 20 to 150 deniers elastic multifilament yarns subjected to a bulking treatment with at least one species of 20 to 100 deniers either elastic or nonelastic multifilament yarns subjected or not subjected to a bulking treatment.

In a method for the production of a vascular prosthesis fabricated in a tubular shape by subjecting yarns to one treatment or a combination of two or more treatments selected from among weaving, knitting, and braiding treatments, the objects described above are accomplished by a method which is characterized by using as the yarn an entangled yarn having fine crimps formed in fibers thereof, wherein the entangled yarn is prepared by subjecting one or more species of elastic yarns subjected to a bulking treatment, a combination of one or more species of elastic yarns subjected to a bulking treatment with one or more species of elastic yarns not subjected to a bulking treatment, or a combination of one or more species of elastic yarns subjected to a bulking treatment with one or more nonelastic yarns subjected or not subjected to a bulking treatment to air jet entangling. In this invention, since entangled yarns furnished with fine looped, spiraled, or coiled crimps are obtained by subjecting a mass of yarns containing in at least part thereof elastic bulked yarns to the air-jet entangling and a tubular fabric is fabricated of these entangled yarns as described above, the produced tubular fabric destined to serve as a vascular prosthesis is furnished on the inner and outer surfaces thereof with large loops resulting from the weaving, knitting, and/or braiding treatments and further furnished in each of the loops with numerous fine crimps originating in the entangled yarns. The vascular prosthesis thus produced, therefore, is endowed with a similar expansibility with that of a natural blood vessel. Since the vascular prosthesis of this invention has countless fine shrinks formed as described above on the inner and outer surfaces thereof, it allows ready attachment thereto of cells and tissues and enjoys high curability. Further, since this vascular prosthesis exhibits as high expansibility as a natural blood vessel, it ideally follows the pulsation of the natural blood vessel, manifests an outstanding resistance to the thrombus, and excels in the patency. Since the tubular fabric is made of such entangled yarns endowed with fine crimps as described above, the woven, knit, and/or braided yarns are entangled so fast that the produced tubular fabric is allowed to retain its shape stably enough to avoid fraying.

Further, in the method of this invention for the production of a vascular prosthesis, since the entangled yarns are endowed with fine crimps in advance of the weaving, knitting, and/or braiding treatment, such characteristic properties of the vascular prosthesis as permeability to water, shape-retaining property, and hardness can be easily adjusted.

The vascular prosthesis of this invention acquires more desirable patency and allow fast attachment thereto of cells and tissues in an embodiment in which the elastic yarns and/or the nonelastic yarns are invariably polyester type yarns, and in another embodiment in which the entangled yarns are obtained by entangling at least one species of 20 to 150 deniers elastic multifilament yarns subjected to a bulking treatment with at least one species of 20 to 100 deniers elastic or nonelastic multifilament yarns subjected or not subjected to a bulking treatment.

In a method for the production of a vascular prosthesis fabricated in a tubular shape by subjecting yarns to one treatment or a combination of two or more treatments selected from among weaving, knitting, and braiding treatments, this invention is directed to the method characterized by using as the yarns mentioned above entangled yarns endowed with fine crimps which are obtained by subjecting to air jet entangling one or more species of elastic yarns subjected to a bulking treatment, a combination of one or more species of elastic yarns subjected to a bulking treatment with one or more species of elastic yarns not subjected to a bulking treatment, or a combination of one or more species of elastic yarns subjected to a bulking treatment with one or more nonelastic yarns subjected or not subjected to a bulking treatment in advance of the weaving, knitting, and/or braiding treatments. Thus, the vascular prosthesis possessed of such outstanding characteristic properties as described above can be easily produced by the method of this invention. Further, in accordance with the method of this invention for the production of a vascular prosthesis, since the entangled yarns are furnished with fine crimps in advance of the weaving, knitting, and/or braiding treatments, such characteristic properties of the produced vascular prosthesis as permeability to water, shape-retaining property, and rigidity or flexibility can be easily adjusted. The vascular prosthesis of this invention, therefore, can be minutely adapted to the site and kind of a natural blood vessel to be substituted.

DETAILED DESCRIPTION OF THE INVENTION

Now, this invention will be described in detail below with reference to embodiments thereof.

The elastic yarn (or mass of elastic fiber(s)) to be used in this invention has no particular restriction except for the requirement that it should exhibit a good stability in vivo. For example, polystyrene type elastic yarns, polyolefin type elastic yarns, etc. are usable, polyester type yarns prove particularly suitable. This invention allows combined use of two or more species of elastic yarns which have been subjected to a bulking treatment or combined use of elastic yarns subjected to a bulking treatment with elastic yarns not subjected, to a bulking treatment and, therefore, remained still in the state of so-called "flat yarns."

The polyester type elastic yarns which are usable herein include not only single-composition polyester type elastic yarns formed of polybutylene terephthalate, polyester-polyether block copolymers, or polyester-polyester copolymers, but also side-by-side complex-composition polyester type yarns between one species of such single-composition polyester type elastic fibers as mentioned above and polyethylene terephthalate, and further polyester type elastic yarns complexed by mixing at least one species of such single-composition polyester type or complex-composition polyester type fibers with polyester fibers (of ordinary grade ), for example. The various species of polyester type elastic yarns enumerated above may be used either singly or in the form of a suitable combination of two or more members.

The polyester-polyether block copolymer type elastic yarns include those made of an aromatic polyester such as polyethylene terephthalate, polyethylene terephthalate/ isophthalate, and poly(1,4-cyclohexane dimethylene terephthalate) as a hard segment and an aliphatic polyether such as polyethylene glycol as a soft segment. As concrete examples thereof, Pelprene-P type (TOYOBO CO., LTD) and Arnitel E.P. (AKZO CO., LTD) may be cited. The polyester-polyester copolymer type elastic yarns include those made of an aromatic polyester such as polyethylene terephthalate, polyethylene terephthalate/isophthalate, and poly(1,4-cyclohexanedimethylene terephthalate) as a hard segment and an aliphatic polyester such as ethylene sebacate as a soft segment. As a concrete example, Pelprene-P type (TOYOBO CO., LTD) may be cited. Of course, the elastic yarns to be used in this invention are not limited in any respect to those specifically cited above.

The term "elastic yarn" as used in this specification refers to yarn which is generally marketed as elastic yarns or to yarn which is possessed of as high elasticity as these commercially available elastic yarns. More specifically, the elastic yarn is desired to be such that the elongation thereof (exclusive of crimped part) required for limiting the elastic recovery ratio from elongation below 90% is not less than 2%, preferably not less than 5%.

The elastic yarn to be used as an essential material in this invention is required to have undergone a bulking treatment. This bulking treatment can be carried out by any of the known methods such as, for example, (1) twisting—heat setting—untwisting, (2) false-twisting, (3) stuffing, (4) scratching, (5) air jetting, and (6) shaping. This treatment is desired to impart to the yarn such expansibility that the CS (crimp stretch) value, i.e. the maximum stretch produced by crimps before the yarn begins to stretch, is not less than 200%, preferably between 300 and 600%.

The nonelastic yarn (or mass of nonelastic fiber(s)) subjected or not subjected to a bulking treatment and used, when necessary, in this invention has no particular restriction except for the requirement that it should exhibit a good stability in vivo. The nonelastic yarns which are effectively usable herein include polyamide type yarns, polyolefin type yarns, and acryl yarns, for example. Fluorine type yarns and polyester type yarns, especially polyester type yarns, are usable particularly advantageously.

The fluorine type yarns which are effectively usable herein include yarns of such compositions as polytetrafluoroethylene, tetrafluoroethylene-hexafluoropropylene copolymer, tetrafluoroethylene-perfluoroalkoxy group copolymers, and tetrafluoroethylene-olefin copolymers, for example. The polyester type yarns which are effectively usable herein include yarns of such compositions as polyethylene terephthalate, poly(1,4-cyclohexanedimethylene terephthalate), and various species of copolymer polyesters containing ethylene terephthalate units, for example. Copolymer polyesters of very numerous compositions have been known to date and they are invariably usable herein.

Representative of these copolymer polyesters are those having such compositions as polyethylene terephthalate/isophthalate, polyethylene terephthalate/sodium 5-sulfonate-isophthalate, polyethylene terephthalate/p-oxybenzoate, and methoxypolyethylene glycol-modified polyethylene terephthalate.

Of course, the nonelastic yarns which are usable, when necessary, in this invention are not limited in any respect to those cited above.

The term "nonelastic yarn" as used in this specification refers to a yarn generally marketed as ordinary yarn or a yarn possessing very low elasticity or virtually no elasticity similarly to such commercially available nonelastic yarns as mentioned above. To be specific, these nonelastic fibers are such that the elongation ratio thereof required for limiting the elastic recovery ratio from elongation below 90% is less than 2%.

The nonelastic yarns which are used, when necessary, in this invention may have not undergone a bulking treatment and, therefore, are still in the state of so-called "flat yarns" or may have undergone a bulking treatment. They are suitably selected, depending on the degree of expansibility to be imparted to a vascular prosthesis intended to be obtained, specifically on the kind of a natural blood vessel to be substituted by the vascular prosthesis and the site of the natural blood vessel. Where the vascular prosthesis is required to have high expansibility, it is permissible to use only the elastic yarns mentioned above and omit the use of these nonelastic yarns. The bulking treatment to be given to the nonelastic yarns can be carried out by any of the known methods enumerated above with respect to the elastic yarns. Again in this case, the yarns resulting from the bulking treatment are desired to acquire expansibility such that the CS value is not less than 200%, preferably between 300 and 600%.

In this invention, one or more species of elastic yarns subjected to a bulking treatment, a combination of one or more species of elastic yarns subjected to a bulking treatment with one or more species of elastic yarns not subjected to a bulking treatment, or a combination of one or more species of elastic yarns subjected to a bulking treatment with one or more species of nonelastic yarns subjected or not subjected to a bulking treatment are entangled in advance of the aforementioned weaving, knitting, and/or braiding treatments for tubular formation and consequently converted into entangled yarns endowed with fine looped, spiraled, or coiled crimps formed in the fibers thereof.

The mass of yarns which is subjected to the entangling treatment described above is only required to contain therein the bulked elastic yarns. Preferably, it contains at least one species of elastic fibers subjected to the bulking treatment and possessed a relatively large size enough to impart necessary elasticity and strength to a vascular prosthesis to be eventually produced and at least one species of elastic fibers or nonelastic fibers subjected or not subjected to the bulking treatment and possessed of a relatively small size enough to allow ready formation of fine crimps. Specifically, the combination of at least one species of elastic yarns subjected to the bulking treatment and possessed of a relatively large size (hereinafter referred to as an "A1 fiber mass") with at least one species of elastic yarns subjected to a bulking treatment and possessed of a relatively small size (hereinafter referred to as an "A2 fiber mass"), the combination of the A1 fiber mass with at least one species of elastic yarns not subjected to a bulking treatment and possessed of a relatively small size (hereinafter referred to as a "B fiber mass"), the combination of the A1 fiber mass with at least one nonelastic yarns subjected to a bulking treatment and possessed of a relatively small size (hereinafter referred to as a "C fiber mass"), the combination of the A1 fiber mass with at least one species of nonelastic raw yarns possessed of a relatively small size (hereinafter referred to as a "D fiber mass"), the combination of the A1 fiber mass with the B fiber mass, the combination of the A1 fiber mass with the A2 fiber mass and the C fiber mass, the combination of the A1 fiber mass with the A2 fiber mass and the D fiber mass, the combination of the A1 fiber mass with the B fiber mass and the C fiber mass, the combination of the A1 fiber mass with the B fiber mass and the D fiber mass, the combination of the A1 fiber mass with the C fiber mass and the D fiber mass, the combination of the A1 fiber mass with the A2 fiber mass, the B fiber mass, and the C fiber mass, the combination of the A1 fiber mass with the A2 fiber mass, the B fiber mass, and the D fiber mass, the combination of the A1 fiber mass with the B fiber mass, the C fiber mass, and the D fiber mass, and the combination of the A1 fiber mass with the A2 fiber mass, the B fiber mass, the C fiber mass, and the D fiber mass may be cited as preferred examples. Of course, this invention allows use of the A1 fiber mass alone, the A2 fiber mass alone, the combination of the A2 fiber mass with the B fiber mass, the combination of the A2 fiber mass with the C fiber mass, the combination of the A2 fiber mass with the D fiber mass, the combination of the A2 fiber mass with the B fiber mass and the C fiber mass, the combination of the A2 fiber mass with the B fiber mass and the D fiber mass, the combination of the A2 fiber mass with the C fiber mass and the D fiber mass, the combination of the A2 fiber mass with the B fiber mass, the C fiber mass and the D fiber mass, for example.

Specifically, the elastic yarns subjected to a bulking treatment and possessed of a relatively large size (A1 yarns) are desired to be multifilament yarns having a size in the range of from 20 to 150 deniers, preferably from 30 to 100 deniers. If the size of the yarns is less than 20 deniers, the tubular fabric to be produced possibly fails to acquire sufficient strength. Conversely, if this size exceeds 150 deniers, the produced tubular fabric acquires high density with difficulty. The species of yarns possessed of a relatively small thickness (A2 yarns, B yarns, C yarns, and D yarns) are specifically desired to be multifilament yarns having a size in the range of from 20 to 100 deniers, preferably from 30 to 75 deniers. If the size of these yarns is less than 20 deniers, the yarns have the possibility of being crimped insufficiently. Conversely, if this size exceeds 150 deniers, the yarns have the possibility of imparting high density to the produced tubular fabric only with difficulty. In each cases, the number of component filaments is generally in the range of from 12 to 48. The ease with which the filaments are entangled increases in proportion as the number of component filaments increases. The number of these filaments is desire to be as large as that of split yarns. This condition, however, constitutes itself no absolute necessity.

In this invention, as a way of entangling one or more species of elastic yarns subjected to a bulking treatment, a combination of one or more species of elastic yarns subjected to a bulking treatment with one or more species of elastic yarns not subjected to a bulking treatment, or a combination of one or more species of elastic yarns subjected to a bulking treatment with one or more nonelastic yarns subjected or not subjected to a bulking treatment, the air jet method is adapted from the viewpoints of uniformity of crimping, expansibility, ease of knitting or weaving of produced entangled yarns, and productivity of the operation.

The "entangled" state formed by the air jet method differs fundamentally from the so-called "entangled" state formed by the covering method. In the "entangled" yarns obtained by the air jet method, outer yarns do not gyrate or twine round inner yarns, but outer yarns and inner yarns are intertwined and are in complete unity. On the contrary, in the so-called "entangled" yarn obtained by the covering method, outer yarns gyrate or twine round inner yarns.

In the so-called entangled yarns obtained by the covering method, if the externally wound yarns are weak, they apt to be caught on and broken by needles of a weaving or knitting device possibly to the extent of impairing productivity of the operation and rendering adjustment of knitting or weaving density and control of porosity difficult. If the externally wound yarns are strong, they tend to impair expansibility of the entangled fibers. These adverse phenomena are not found in the entangled yarns obtained by the air jet method.

The basic principle of the entangling by the air jet method resides in exposing two or more filament bundles to a turbulent flow of air jet thereby causing the individual filaments to be separated from one another and, at the same time, to be vigorously moved about within the turbulent flow of air current and, by a subsequent simple operation of continuously extracting the filaments in a tensionless state from the zone of the turbulent flow of air jet, enabling the filaments at the instant of the extraction thereof from the stirring device to slacken and assume a crimped bulky state in which fine looped, spiraled, and coiled crimps mingle irregularly.

In this invention, from the entangled yarns obtained as described above, the vascular prosthesis is obtained by subjecting the entangled yarns to one treatment or a combination of two or more treatments selected from among weaving, knitting, and braiding treatments thereby converting them into a tubular fabric as generally practiced. As respects the construction of the tubular fabric, the constructions obtained by warp knitting, weft knitting, triaxial knitting, hollow weave, and braid knitting are conceivable. This invention does not discriminate one tubular fabric from another due to the difference of the fabrication. The vascular prosthesis of this invention which is obtained as described above is furnished on the inner and outer wall surfaces thereof with countless fine crimps and is possessed of expansibility approximating that of a natural blood vessel. This expansibility fulfills the condition that the elongation in the radial direction is in the range of from 2 to 15%, preferably from 5 to 15%, and the elongation in the axial direction is in the range of from 2 to 20%, preferably from 5 to 15% under the typical load of an inner pressure of 150 mmHg. When the vascular prosthesis of this invention having the expansibility defined above is implanted into a body, it ideally follows the pulsation of the natural blood vessel and therefore shows antithrombogenicity.

The diameter of the vascular prosthesis of this invention can be freely selected in a wide range approximately between 4 and 30 mm, depending on the site of and kind of use. Particularly in the case of the vascular prosthesis of this invention, since it exhibits a highly desirable patency, it fulfills its function sufficiently even when the diameter is approximately in the range of from 4 to 6 mm, for example. Although the permeability to water of the vascular prosthesis of this invention is not particularly restricted, it is desired to be approximately in the range of from 100 to 10,000 cc/min./cm$^2$-120 mmHg, preferably from 500 to 3,000 cc/min./cm$^2$-120 mmHg.

The use of the vascular prosthesis of this invention is obtained by a method which comprises implanting the vascular prosthesis in a sterilized state directly in a host's vital system and causing cells and tissues to attach thereto or by a method which comprises collecting cells from the wall of a host's blood vessel under an aseptic condition, seeding the cells on the vascular prosthesis in a sterilized state in vitro, reconstructing the surfaces of the vascular prosthesis functionally and structurally, and transplanting the reconstructed vascular prosthesis to the host for further growth in vivo of the seeded cells. The vascular prosthesis, when necessary, may be subjected to any of the conventionally known surface treatments such as heparinizing treatment, gelatinizing treatment, collagen treatment, albuminizing treatment, and fibrin treatment which are intended to give antithrombogenicity.

EXAMPLES

Now, this invention will be described more specifically below with reference to working examples. It should be noted, however, that this invention is not limited in any sense to or by the following examples.

EXAMPLE 1

An polybutylene terephthalate-polyethylene terephthalate conjugate elastic yarn (50-deniers/24-filaments, a proprietary product of KURARAY CO., LTD marketed under trademark designation of "Artron") was given a CS value of 350% by a bulking treatment of the false twisting method. Separately, ordinary polyester yarn (30-deniers/ 24-filaments, a proprietary product of KANEBO, LTD) were given a CS value of 400% by a bulking treatment of the false twisting method. Stretched finely crimped processed yarn (1) was produced by exposing the resultant bulked polybutylene terephthalate-polyethylene terephthalate conjugate elastic fibers and the resultant bulked ordinary polyester fibers to a turbulent flow of jet air in an air jet crimping device (produced by AIKI SEISAKUSYO LTD and marketed under product code of "AT-501 TYPE EXII") thereby disturbing and entangling the fibers of these yarns in finely looped, spiraled, and coiled states.

In the entangling treatment, the feeding ratio of the bulked polybutylene terephthalate-polyethylene terephthalate conjugate elastic yarn was fixed at +20%, the feeding ratio of the bulked polyester yarn at +60%, and the winding to feeding ratio at −15%.

Figure 1:
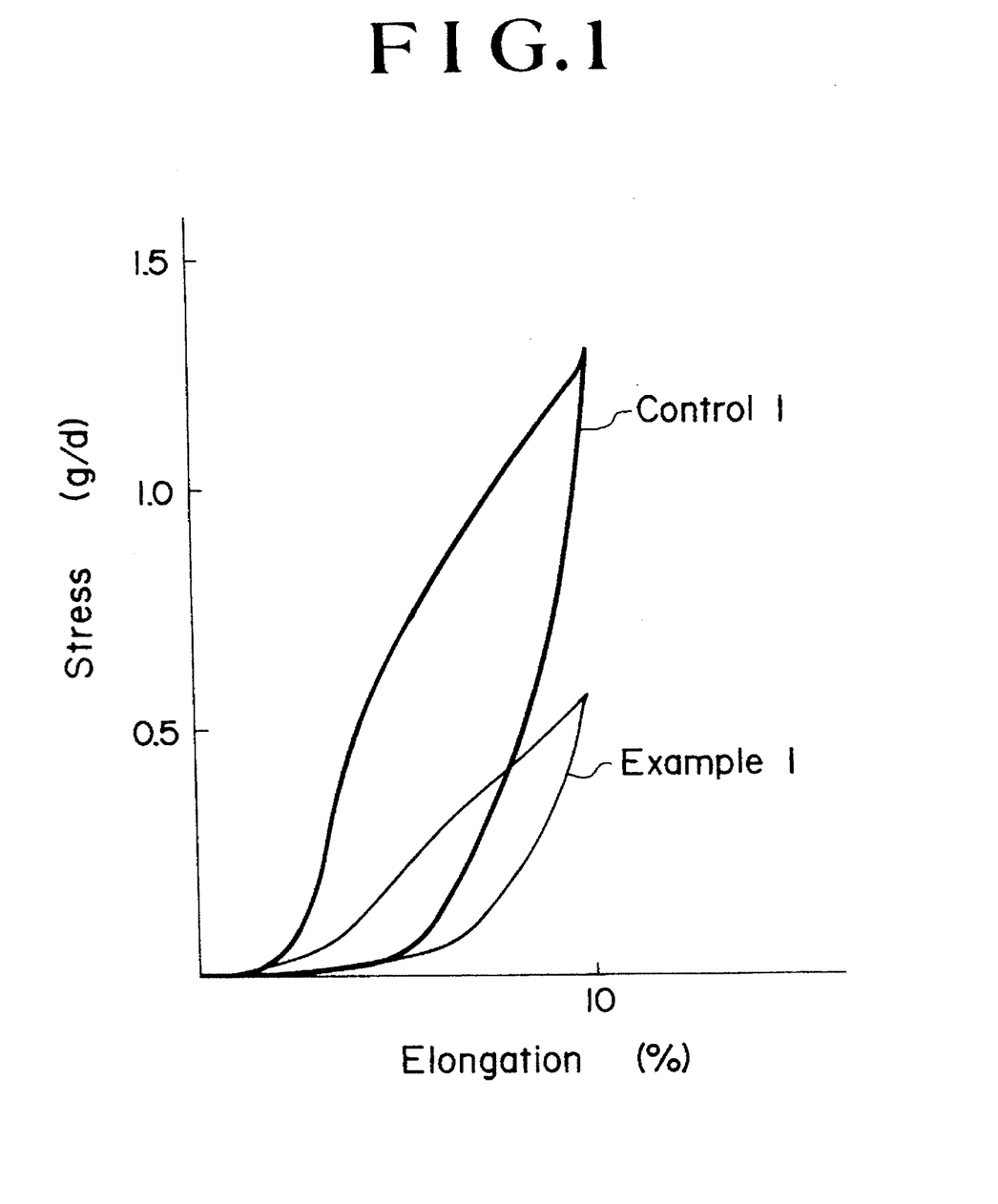
FIG. 1 is a graph showing the curve of a recovery ratio from elongation of an elastic finely crimped processed yarn used in a vascular prosthesis as one embodiment of this invention and the curve of a recovery ratio from elongation of an ordinary polyester fiber subjected to a bulking treatment and used in a vascular prosthesis prepared in a control.
Figure 2:
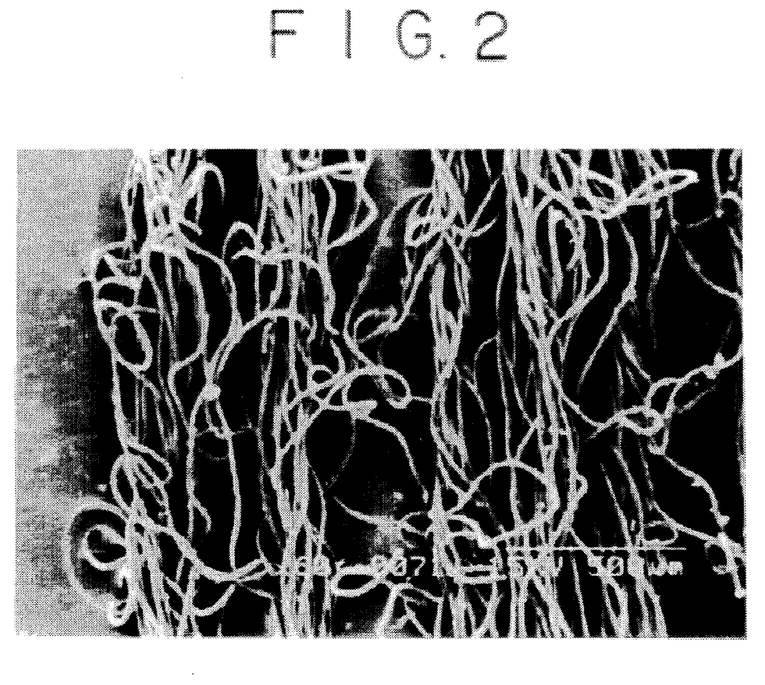
FIG. 2 is a scanning electron microphotograph of the elastic finely crimped processed yarns used in the vascular prosthesis as one embodiment of this invention.

In the stretched finely crimped processed yarn (1) consequently obtained, the individual fibers were finely crimped in a looped, spiraled, or coiled state. The stretched finely crimped processed yarn (1) had a fineness of 100 deniers/48 filaments and exhibited outstanding expansibility. The curve of elongation recovery ratio of these stretched finely crimped processed yarn is shown in FIG. 1. The elastic recovery ratio of the stretched finely crimped processed yarn (1) from elongation at an elongation ratio of not more than 7% was not less than 90%. FIG. 2 represents a scanning electron microphotograph (60 magnifications) of the stretched finely crimped processed yarn (1).

Then, from the stretched finely crimped processed yarns (1), a tubular fabric was produced by the use of a 30-gauge double-raschel machine. The tubular fabric was formed in a back half stitch.

Figure 4:
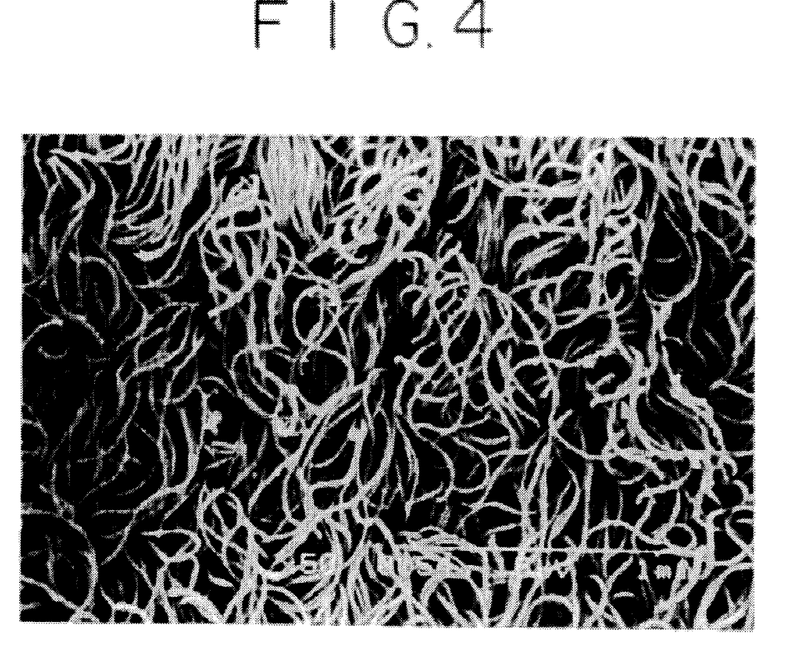
FIG. 4 is a scanning electron microphotograph of an inner wall surface of the vascular prosthesis as one embodiment of this invention.

The tubular fabric was turned inside out, scoured, and crimped to produce a vascular prosthesis 6 mm in inside diameter. The knitting ratio of the produced vascular prosthesis was 65 loops/inch in the longitudinal direction and 43 loops/inch in the lateral direction and the permeability to water thereof was 3,000 cc/min./cm$^2$-120 mmHg. The expansibility of the vascular prosthesis was such that the elongation ratio in the radial direction was 8% and the elongation ratio in the axial direction was 7% under the load of an inner pressure of 150 mmHg. The produced vascular prosthesis had numerous fine crimps formed on the inner and outer wall surfaces thereof and a stable texture sparingly susceptible of disintegration. FIG. 4 represents a scanning electron microphotograph (50 magnifications) of the inner wall surface of this vascular prosthesis.

EXAMPLE 2

Polyester-polyether block copolymer elastic yarn (75-deniers/24-filaments, a proprietary product of DU PONT-TORAY CO., LTD marketed under trademark designation of "Hytrel") was given a CS value of 380% by a bulking treatment of the false twisting method. Separately, ordinary polyester yarn (30-deniers/24-filaments, a proprietary product of KANEBO, LTD) was given a CS value of 400% by a bulking treatment of the false twisting method. Stretched finely crimped processed yarn (2) was produced by exposing the resultant bulked polyester-polyether block copolymer elastic yarn and the resultant bulked ordinary polyester yarn to a turbulent flow of air jet by the use of an air jet crimping device (produced by AIKI SEISAKUSYO LTD marketed under product code of "AT-501 TYPE EXII) thereby disturbing and entangling the fibers of these yarns in a looped, spiraled, and coiled shape.

In the entangling treatment, the feeding ratio of the bulked polyester-polyether block copolymer elastic yarn was fixed at +15% and that of the feeding ratio of the bulked polyester yarn was fixed at +50% and the winding to feeding ratio was fixed at −11%.

In the stretched finely crimped processed yarn (2) thus produced, the individual fibers were finely crimped in a looped, spiraled, and coiled state. The fineness of the stretched finely crimped processed yarn (2) was 120 deniers/48 filaments. The elastic recovery ratio of the stretched finely crimped processed yarn (2) from elongation at an elongation ratio of not more than 10% was not less than 90%.

Then, a tubular fabric was produced from the stretched finely crimped processed yarns (2) by the use of a 30-gauge double-raschel machine. This tubular fabric was formed in a double-denbigh stitch.

Then, from the tubular fabric, a vascular prosthesis was produced by subjecting this tubular fabric to scouring and crimping treatments. The knitting density of the produced vascular prosthesis was 58 loops/inch in the longitudinal direction and 42 loops/inch in the lateral direction and the permeability to water thereof was 2,500 cc/min./cm$^2$-120 mmHg. The expansibility of the vascular prosthesis was such that the elongation ratio in the radial direction was 8% and that in the axial direction was 8% under the load of an inner pressure of 150 mmHg. The produced vascular prosthesis had numerous fine crimps formed on the inner and outer wall surfaces thereof and a stable texture sparingly susceptible of disintegration.

EXAMPLE 3

Polyester-polyester copolymer elastic yarn (75-deniers/24-filaments, a proprietary product of TOYOBO CO., LTD marketed under trademark designation of "Pelprene") was given a CS value of 320% by a bulking treatment of the false twisting method. Stretched finely crimped process yarn (3) was produced by exposing the resultant bulked polyester-polyether block copolymer elastic yarn and an ordinary polyester flat yarn (30-deniers/24-filaments, a proprietary product of KANEBO, LTD) to a turbulent flow of air jet by the use of an air jet crimping device (produced by AIKI SEISAKUSYO LTD and marketed under product code of "AT-501 TYPE EXII) thereby disturbing and entangling the individual fibers of these yarns in the form of finely looped, spiraled, and coiled crimps.

In the entangling treatment, the feeding rate of the bulked polyester-polyester copolymer elastic yarn was fixed at +10% and the feeding rate of the polyester flat yarn at 30%, and the winding to feeding rate at −5%.

In the stretched finely crimped processed yarn (3) consequently obtained, the individual fibers were finely crimped in looped, spiraled, and coiled states. The fineness of the stretched finely crimped processed yarn (3) was 115-deniers/48-filaments. The elastic recovery ratio of the stretched finely crimped processed yarn (3) from elongation at an elongation ratio of not more than 8% was not less than 90%.

From the stretched finely crimped processed yarns (2), a tubular fabric was produced by the use of a 30-gauge double-raschel machine. It was constructed in a back half stitch.

Then, from this tubular fabric, a vascular prosthesis 6 mm in inside diameter was produced by turning the tubular fabric inside out, sourcing it, and subjecting it to a crimping treatment. The knitting density of this vascular prosthesis was 60 loops/inch in the longitudinal direction and 42 loops/inch in the lateral direction and the permeability to water of the vascular prosthesis was 2,800 cc/min./cm$^2$-120 mmHg. The expansibility of the vascular prosthesis was such that the elongation in the radial direction was 10% and the elongation in the axial direction was 11% under the load of an inner pressure of 150 mmHg. The vascular prosthesis thus produced had numerous fine crimps formed on the inner and outer wall surfaces thereof and showed a stable texture sparingly susceptible of disintegration.

Control 1

Figure 3:
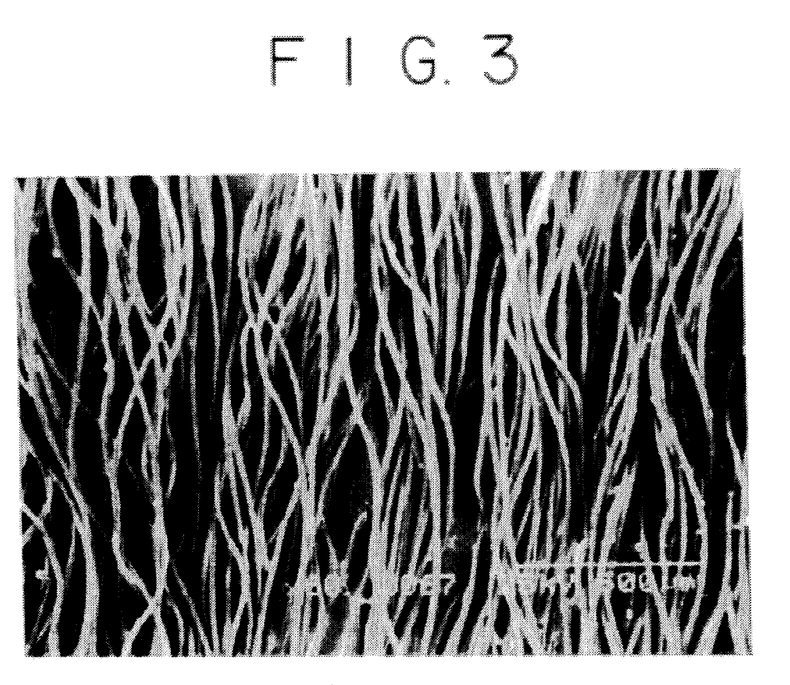
FIG. 3 is a scanning electron microphotograph of the ordinary polyester yarns subjected to a bulking treatment and used in the vascular prosthesis prepared in the control.

An ordinary polyester yarn (100-deniers/36-filaments, a proprietary product of TOYOBO CO., LTD) was given a CS value of 400% by a bulking treatment of the false twisting method. FIG. 1 shows the curve of recovery ratio from elongation of the stretched finely crimped processed yarn (1) obtained in Example 1 together with the curve of recovery ratio from elongation of the resultant bulked ordinary polyester yarn for the purpose of comparison. FIG. 3 shows a scanning electron microphotograph (60 magnifications) of the bulked ordinary polyester yarns.

Then, from the bulked ordinary polyester yarns, a tubular fabric was produced by the use of a 30-gauge double-raschel machine.

Figure 5:
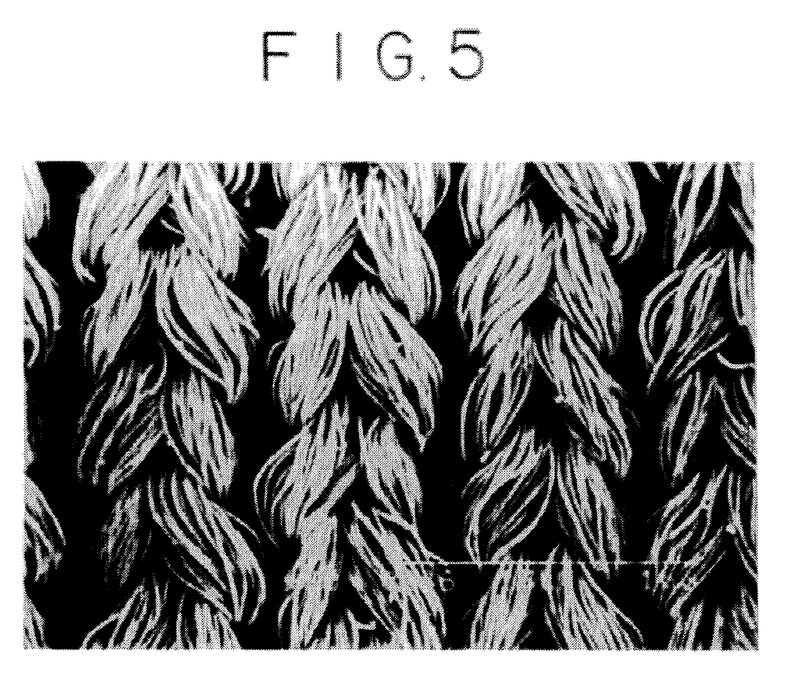
FIG. 5 is a scanning electron microphotograph of an inner wall surface of the vascular prosthesis prepared in the control.

A vascular prosthesis was produced by turning the tubular fabric inside out, scouring it, and subjecting it to a crimping treatment. The knitting density of the produced vascular prosthesis was 64 loops/inch in the longitudinal direction and 48 loops/inch in the lateral direction and the permeability to water of the vascular prosthesis was 3,400 cc/min./cm$^2$-120 mmHg. The expansibility of this vascular prosthesis was such that the elongation in the radial direction was 0% and the elongation in the axial direction was 1% under the load of an inner pressure of 150 mmHg. FIG. 5 shows a scanning electron microphotograph (50 magnitudes) of the inner wall surface of the vascular prosthesis consequently produced.

EXAMPLE 4

A graft of the vascular prosthesis (6 mm in inside diameter and 5 cm in length) produced in Example 1 was implanted to the carotid artery in a mongrel dog. It was sterilized and then subjected to a preclotting treatment with the blood collected from the host dog in advance of the implantation. During the suturing operation in the process of implantation, the needle easily pierced into the vascular prosthesis and no sign of disintegration of fibers was found at the cut edges of the vascular prosthesis graft. When the anastomosed vascular prosthesis graft was excised from the dog after one month's standing therein, the graft was observed to have no ectasis, the inner wall of the graft was observed to be invaded by cellular components, and the surface of the graft exposed to the flow of blood was covered thoroughly by endothelial cells. No intimal hyperplasia was detected in the anastomotic portion or the whole length of the graft.

When grafts of the vascular prostheses produced in Example 2 and Example 3 were implanted each to the carotid artery of a mongrel hybrid dog and observed in the same manner as described above, substantially similar desirable results were obtained.

Control 2

A graft of the vascular prosthesis (6 mm in inside diameter and 5 cm in length) produced in Control 1 was subjected to a preclotting treatment and then implanted to the carotid artery of a mongrel dog in the same manner as in Example 4. When the graft was excised from the dog after one month's standing therein and examined, local adhesion of thrombi was recognized on the inner wall surface of the graft, indicating that no sufficient organization of the graft was attained during the standing. Slight hyperplasia was detected in the anastomotic site, indicating the possibility of the occlusion of the graft after a long implantation period.

We claim:

1. A vascular prosthesis comprising a tubular fabric adapted for direct contact with blood and the passage of blood therethrough, said fabric comprising yarn entangled prior to being formed into said fabric, wherein said entangled yarn is obtained by entangling an elastic yarn with one of another elastic yarn and a nonelastic yarn, wherein the elongation ratio of said vascular prosthesis is in the range of from 2 to 15% in the radial direction and 2 to 20% in the axial direction under the load of an inner pressure of 150 mmHg, and wherein said tubular fabric is fabricated by a process selected from the group consisting of weaving, knitting and combinations thereof.

* * * * *

UNITED STATES PATENT AND TRADEMARK OFFICE
CERTIFICATE OF CORRECTION

PATENT NO. : 5,476,507
DATED : December 19, 1995
INVENTOR(S) : Sobei WAKABAYASHI et al It is certified that error appears in the above-indentified patent and that said Letters Patent is hereby corrected as shown below:

In Column 12, line 13, delete "30%" and insert -- +30% --.

Signed and Sealed this

Twelfth Day of March, 1996

Attest:

BRUCE LEHMAN

Attesting Officer    Commissioner of Patents and Trademarks